US012708559B2

(12) United States Patent
Govari et al.

(10) Patent No.: US 12,708,559 B2
(45) Date of Patent: Aug. 18, 2026

(54) VITRECTOR WITH DISPOSABLE CUTTER

(71) Applicant: JOHNSON & JOHNSON SURGICAL VISION, INC., Irvine, CA (US)

(72) Inventors: Assaf Govari, Haifa (IL); Alexander Shechtman, Haifa (IL); Ilya Sitnitsky, Nahariya (IL); Stanislav Katzir, Hadera (IL); Elad Avraham Diukman, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 648 days.

(21) Appl. No.: 18/086,808

(22) Filed: Dec. 22, 2022

(65) Prior Publication Data

US 2024/0207095 A1 Jun. 27, 2024

(51) Int. Cl.
*A61F 9/007* (2006.01)

(52) U.S. Cl.
CPC ................................ *A61F 9/00763* (2013.01)

(58) Field of Classification Search
CPC .. A61F 9/007; A61F 9/00736; A61F 9/00763; A61M 1/77; A61M 1/774; A61B 17/32; A61B 17/320016; A61B 2017/0023; A61B 2017/0046; A61B 2017/00477
See application file for complete search history.

(56) References Cited

U.S. PATENT DOCUMENTS

| | | | |
|---|---|---|---|
| 3,559,970 A | 2/1971 | Hamabe et al. | |
| 3,882,872 A | 5/1975 | Douvas et al. | |
| 4,014,342 A | 3/1977 | Staub et al. | |
| 4,246,902 A | 1/1981 | Martinez | |
| 4,314,560 A | 2/1982 | Helfgott et al. | |
| 4,320,761 A * | 3/1982 | Haddad | A61F 9/00763 408/58 |
| 4,768,506 A | 9/1988 | Parker et al. | |
| 5,279,547 A | 1/1994 | Costin | |
| 5,403,276 A | 4/1995 | Schechter et al. | |
| 5,417,246 A | 5/1995 | Perkins et al. | |
| 5,549,139 A | 8/1996 | Perkins et al. | |
| 5,716,363 A | 2/1998 | Josephberg | |
| 5,788,667 A | 8/1998 | Stoller | |
| 5,857,485 A | 1/1999 | Perkins et al. | |
| 5,979,494 A | 11/1999 | Perkins et al. | |
| 6,010,496 A | 1/2000 | Appelbaum et al. | |
| 6,258,111 B1 | 7/2001 | Ross et al. | |
| 6,290,690 B1 | 9/2001 | Huculak et al. | |
| 6,506,176 B1 | 1/2003 | Mittelstein et al. | |
| 6,527,736 B1 | 3/2003 | Attinger et al. | |
| 6,575,990 B1 | 6/2003 | Wang et al. | |
| 6,599,271 B1 | 7/2003 | Easley | |
| 6,599,277 B2 | 7/2003 | Neubert | |

(Continued)

FOREIGN PATENT DOCUMENTS

| | | |
|---|---|---|
| DE | 10300127 A1 | 7/2004 |
| WO | 2008079526 A2 | 7/2008 |

(Continued)

*Primary Examiner* — Robert A Lynch

(57) ABSTRACT

Methods and systems provide a disposable cutting section which is removably attachable from a multiple use motor section, to form a handpiece for use in ophthalmic procedures, such as vitrectomies. The motor section includes a motor for driving a needle of the cutting section.

15 Claims, 5 Drawing Sheets

(56) References Cited

U.S. PATENT DOCUMENTS

| | | | |
|---|---|---|---|
| 6,689,089 | B1 | 2/2004 | Tiedtke et al. |
| 6,939,341 | B2 | 9/2005 | Vijfvinkel |
| 7,335,217 | B2 | 2/2008 | Wang et al. |
| 8,298,253 | B2 | 10/2012 | Charles |
| 8,460,324 | B2 | 6/2013 | Gerg et al. |
| 8,818,564 | B2 | 8/2014 | Zhou et al. |
| 8,986,332 | B2 | 3/2015 | Gerg et al. |
| 9,271,867 | B2 | 3/2016 | Lynn et al. |
| 9,486,358 | B2 | 11/2016 | Lee et al. |
| 9,498,376 | B2 | 11/2016 | Lee et al. |
| 9,597,228 | B2 | 3/2017 | Lynn et al. |
| 9,750,639 | B2 | 9/2017 | Barnes et al. |
| 9,775,742 | B2 | 10/2017 | Hajishah et al. |
| 10,307,291 | B2 | 6/2019 | Lee et al. |
| 10,758,411 | B2 | 9/2020 | Dean et al. |
| 10,881,549 | B2 | 1/2021 | Lee et al. |
| 11,241,335 | B2 | 2/2022 | Carter et al. |
| 11,376,157 | B2 | 7/2022 | Lee et al. |
| 2001/0029335 | A1 | 10/2001 | Juan et al. |
| 2002/0173814 | A1 | 11/2002 | Jung et al. |
| 2003/0195538 | A1 | 10/2003 | Wang et al. |
| 2005/0096682 | A1 | 5/2005 | Daffer |
| 2005/0113715 | A1 | 5/2005 | Schwindt et al. |
| 2007/0078506 | A1 | 4/2007 | McCormick et al. |
| 2007/0088376 | A1 | 4/2007 | Zacharias |
| 2008/0114372 | A1 | 5/2008 | Edwards et al. |
| 2008/0146988 | A1 | 6/2008 | Olivera et al. |
| 2008/0154292 | A1 | 6/2008 | Huculak et al. |
| 2008/0188881 | A1 | 8/2008 | Chon |
| 2008/0208207 | A1 | 8/2008 | Huculak et al. |
| 2008/0208233 | A1 | 8/2008 | Barnes et al. |
| 2009/0143734 | A1 | 6/2009 | Humayun et al. |
| 2009/0259242 | A1 | 10/2009 | Gerg et al. |
| 2010/0156646 | A1 | 6/2010 | Cull et al. |
| 2011/0054508 | A1 | 3/2011 | Zhou et al. |
| 2011/0077626 | A1 | 3/2011 | Baerveldt et al. |
| 2011/0144675 | A1 | 6/2011 | Gao et al. |
| 2011/0295293 | A1 | 12/2011 | Agahi |
| 2011/0295296 | A1 | 12/2011 | Charles |
| 2012/0053486 | A1 | 3/2012 | Huculak |
| 2012/0157879 | A1 | 6/2012 | Mark et al. |
| 2012/0157906 | A1 | 6/2012 | Underwood et al. |
| 2012/0158029 | A1 | 6/2012 | Underwood et al. |
| 2012/0158030 | A1 | 6/2012 | Underwood et al. |
| 2012/0165724 | A1 | 6/2012 | Auld et al. |
| 2012/0310146 | A1 | 12/2012 | Easley |
| 2013/0060210 | A1 | 3/2013 | Ross et al. |
| 2013/0144317 | A1 | 6/2013 | Valencia |
| 2013/0158578 | A1 | 6/2013 | Ghodke et al. |
| 2014/0114336 | A1 | 4/2014 | Schmitz et al. |
| 2014/0171991 | A1 | 6/2014 | Lee et al. |
| 2014/0171993 | A1 | 6/2014 | Lynn et al. |
| 2015/0148836 | A1 | 5/2015 | Heeren |
| 2017/0319387 | A1 | 11/2017 | Barnes et al. |
| 2020/0289319 | A1 | 9/2020 | Carter et al. |
| 2020/0360185 | A1* | 11/2020 | Carter .................. A61M 1/774 |
| 2021/0154004 | A1* | 5/2021 | Dockhorn ............. A61F 2/1672 |

FOREIGN PATENT DOCUMENTS

| | | | |
|---|---|---|---|
| WO | 2011149621 | A1 | 12/2011 |
| WO | 2014099982 | A1 | 6/2014 |
| WO | 2014099993 | A1 | 6/2014 |
| WO | 2014105531 | A1 | 7/2014 |

* cited by examiner 10
22
LA
40
19
18
14

72
70
22
80t
74
54a
54
60c
84
22x
60b
22y
60a
80
50
18p
18b
53
52
18p
60
18c
18a
58
40
18y
56
52a
19
18
38
18a
40
36a
38x
30p
34
48
46
14
30
35
32
30d

VITRECTOR WITH DISPOSABLE CUTTER

TECHNICAL FIELD

This disclosure relates generally to vitrectomy, and specifically to tools used for vitrectomy.

BACKGROUND

Vitrectomy is surgery that removes vitreous humor from an eye, and the surgery is performed using a vitrector, which comprises a hollow needle through which the vitreous humor is aspirated. A vitrector is used in eye surgery to remove vitreous humor from the eye. The removal is based on back-and-forth and linear motion of a cutting needle within an external casing including a window, and suction through the cutting needle. Conventional vitrectors are pneumatic. The back-and-forth motion is achieved with a compressor delivering pulses of compressed air and a diaphragm.

During operation of the vitrector, the needle is oscillated within the casing, and the oscillation causes the distal tip of the needle to cut the vitreous humor as the tip traverses the window. The cut portions of the vitreous humor are subsequently aspirated, via an aspiration line, through which suction is pulled.

SUMMARY OF THE DISCLOSURE

The present disclosed devices and methods for their use, include a disposable cutting section which is removably attachable from a multiple use motor section, to form a handpiece for use in ophthalmic procedures, such as a vitrector for performing vitrectomies. The motor section includes a motor for driving a needle of the cutting section.

The present disclosed subject matter divides a vitrector into a disposable cutting section including a cutting needle and aspiration line, and a permanent motor section including a motor and shaft. The two sections are coupled, as a disposable shaft of the coupling element in the cutting section, receives the motor shaft, in a frictionally snug manner, while allowing coupling and separation of the cutting section and the motor section easily by manual forces of human hands. As the cutting section lacks a motor or other expensive components, the disposable cutting unit is cost effective, as expensive motors and associated motor components are in a separate and reusable motor housing.

BRIEF DESCRIPTION OF THE DRAWINGS

Some examples of the disclosure are herein described with reference to the accompanying drawings, where like reference numerals or characters represent corresponding or like elements. Dimensions of components and features shown in the figures are chosen for convenience and clarity of presentation and are not necessarily shown to scale.

The drawings are as follows.

DESCRIPTION OF EXAMPLES

Overview

Figures 1, 2A:
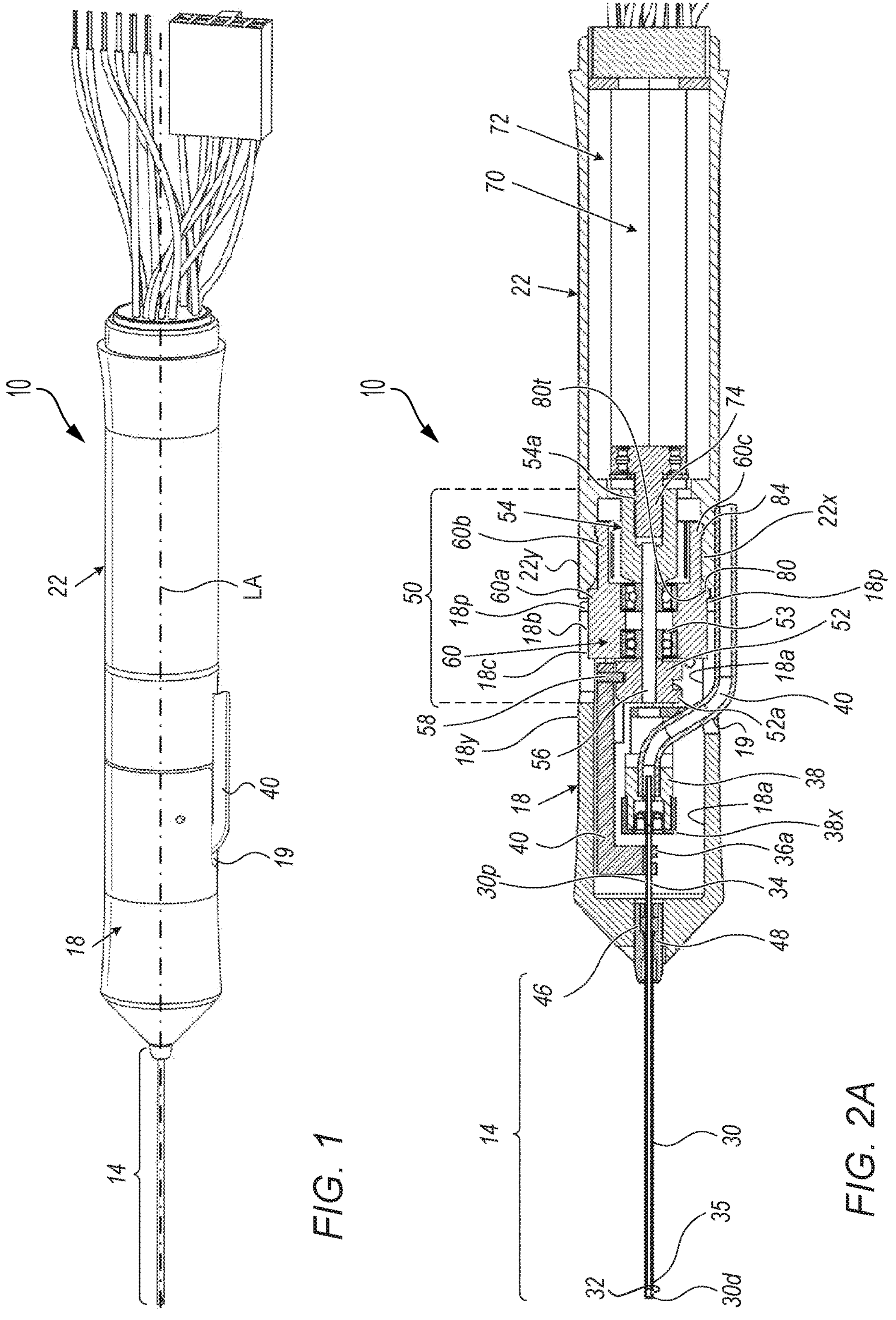
FIG. 1 is a side view of the handpiece with the disposable needle housing joined to the permanent motor housing, in accordance with the disclosure.
FIG. 2A is a cross-sectional view of the handpiece of FIG. 1, with the disposable needle housing separated from FIG. 2B is a cross sectional view of the internal components of the needle housing in detail.

Vitrectors are expensive devices. Most of the vitrectors are pneumatic devices, with some being electromechanical devices. Typically, the entire vitrector, including the motor and drive mechanism is single use. This is wasteful, as the motor and its associated mechanisms and circuitry bear a substantial part of the bill of materials.

Attempts to make portions of the electromechanical vitrectors single use and disposable, to be more cost efficient, have met difficulty. This is due to the motor section being part of the disposable portion, such that costs remain high.

To have a motor section, separate from a cutting section, which includes the cutting needle, for an electromechanical vitrector presents challenges. These challenges include easy engagement and disengagement of the motor section from the cutting section, by human hands connecting and disconnecting cutting and motor sections, while a shaft of the motor of the motor section is well fitted in shaft coupler of a driver of the cutting section in a friction fit without slippage between the motor shaft and the shaft coupler, such that the rotational motion from the motor is efficiently transferred to the driver. This transferred rotational motion to the driver is translated via a cam of the driver into translational or linear motion for a cutting needle of the cutting section.

According to some example embodiments, portions of the vitrector have been made disposable, and for a single use, while other portions may be reused, for example, once sterilized and the like, so that these portions may be safely reused. In this manner the vitrector device may be more cost effective, than those presently available.

The electromechanical vitrector of the disclosure includes a handpiece, formed of two sections, a disposable cutting section and a motor section. The disposable cutting section couples to the motor section, which is reusable, and includes a motor. The coupling is such that rotational motion from the motor is transferred from a motor shaft, rotated by the motor, to a shaft coupler of the disposable cutting section. The rotational motion on the shaft coupler is translated or converted to linear (back and forth) motion of the needle of the cutting section.

The shaft coupler of the cutting section is correspondingly configured and shaped to receive the motor shaft and engage the motor shaft, such that the motor shaft couples with the shaft coupler. This engagement is augmented by the shaft coupler being of a silicon material which provides friction with the of a desired hardness, motor shaft, such that the engagement is frictionally snug, and provides sufficient frictional forces which prevent or minimize slippage in a rotational direction, resulting in maximum rotational motion transfer from the motor shaft to the driver. These same frictional forces are low enough to provide low resistance when pulling the motor shaft in and out of the coupler, when engaging or separating the cutting section and the motor section from each other.

The disposable cutting section may be disengaged from the motor section at the end of a procedure and, the motor section reconnected with a new disposable cutting section, to maintain sterility.

The motor section may also include an additional locking mechanism, for locking to the cutting section. The motor section is designed to receive a correspondingly configured portion of the disposable cutting section, to augment the maintenance of the connection between the motor section and the disposable cutting section.

System Description

Throughout this document, references are made to directions and orientations, such as inward, outward, upper, lower, front, rear, top, bottom, lateral, proximal, distal, central, and derivatives thereof, and the like. The references to these directions and orientations are exemplary, for describing and explaining the present invention, and embodiments thereof, and are not limiting in any way.

FIG. 1 shows a side view of the handpiece 10, for example, used a part of a vitrector, for controlling a needle (also known as a "cutting needle") 14, extending from the needle housing section (needle housing or cutting section) 14 (the terms "needle housing section", "needle hosing" and "cutting section" are used interchangeably herein). The handpiece 10 is separable, with the needle housing 18 being a first section, which is removably attachable (e.g., removably connected or removably coupled) from a motor housing section, being a second section or motor housing 22. The needle housing 18 is disposable or single use, while the motor housing 22, is permanent or multi-use. In this arrangement, when the needle housing 18 is connected or coupled to the motor housing 22, such that the motor 70 of the motor housing 22 is mechanically coupled to the cutting section 18, and ultimately, the cutting needle 14. A longitudinal axis LA extends through the handpiece 10.

FIG. 2A shows the handpiece 10 with the sections 18, 22 joined or otherwise attached or connected. The sections 18, 22 include the needle housing section 18, and the motor housing section 22.

Figure 2B:
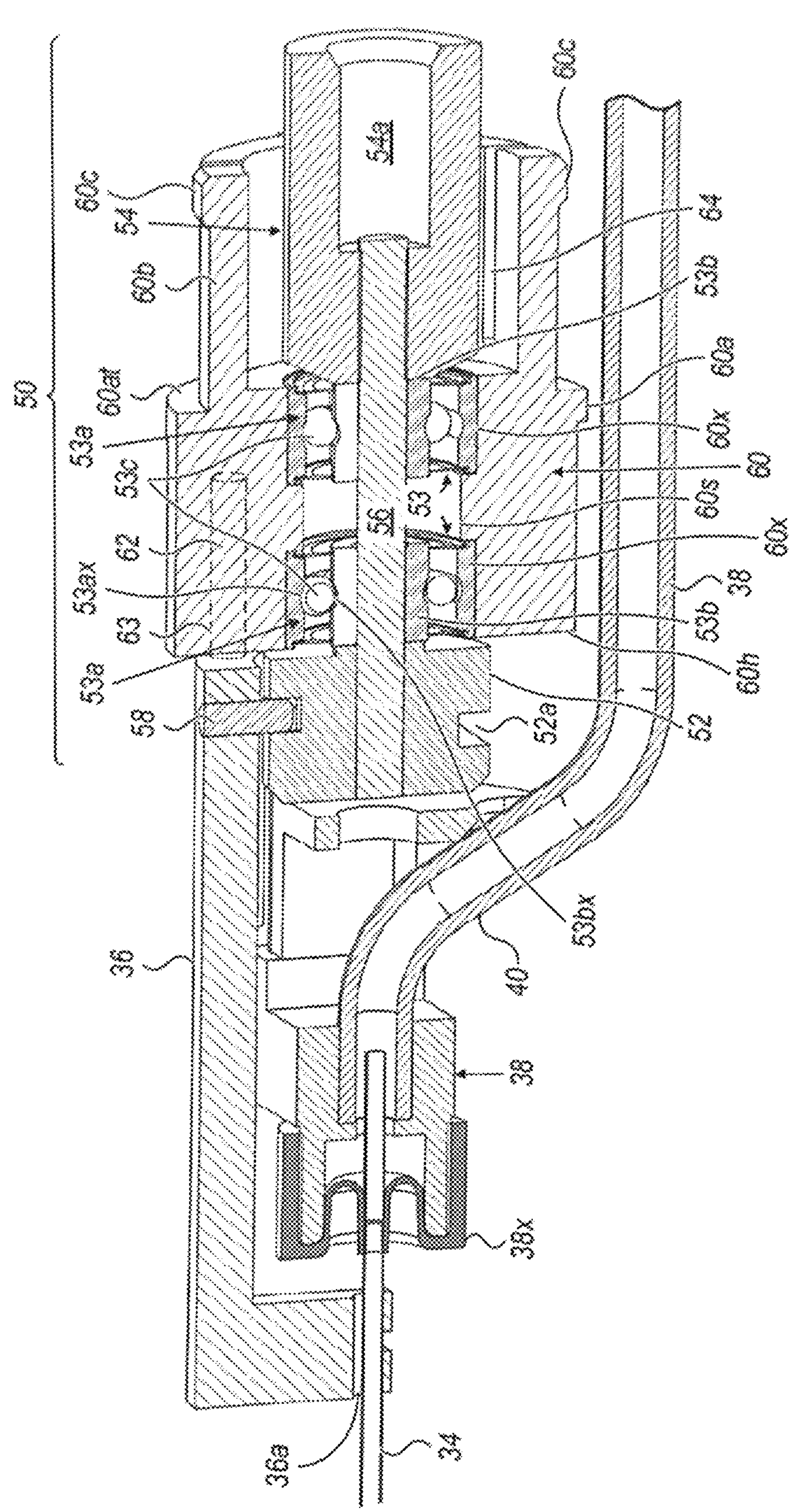
Figure 3:
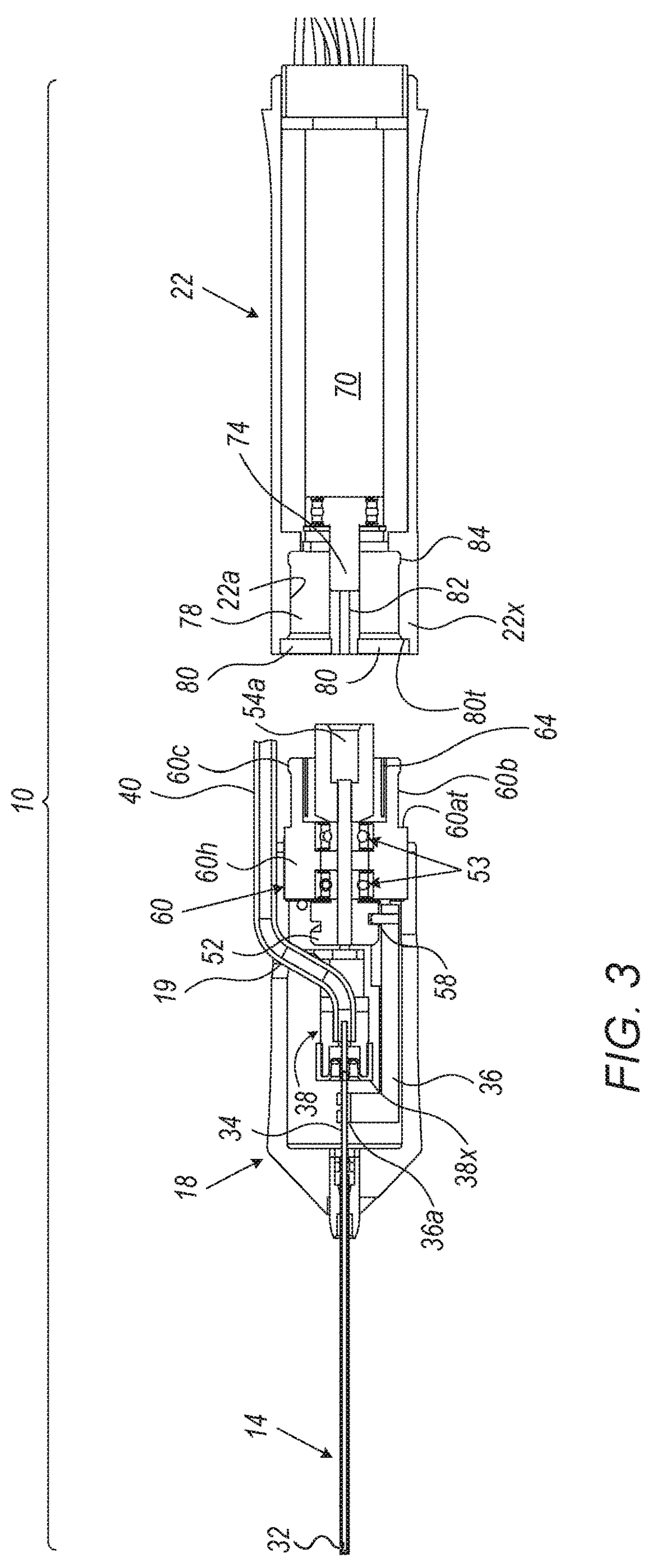
FIG. 3 is a cross sectional view of the handpiece of FIG. 1 shown with needle hosing separated from the motor housing.
Figure 5A:
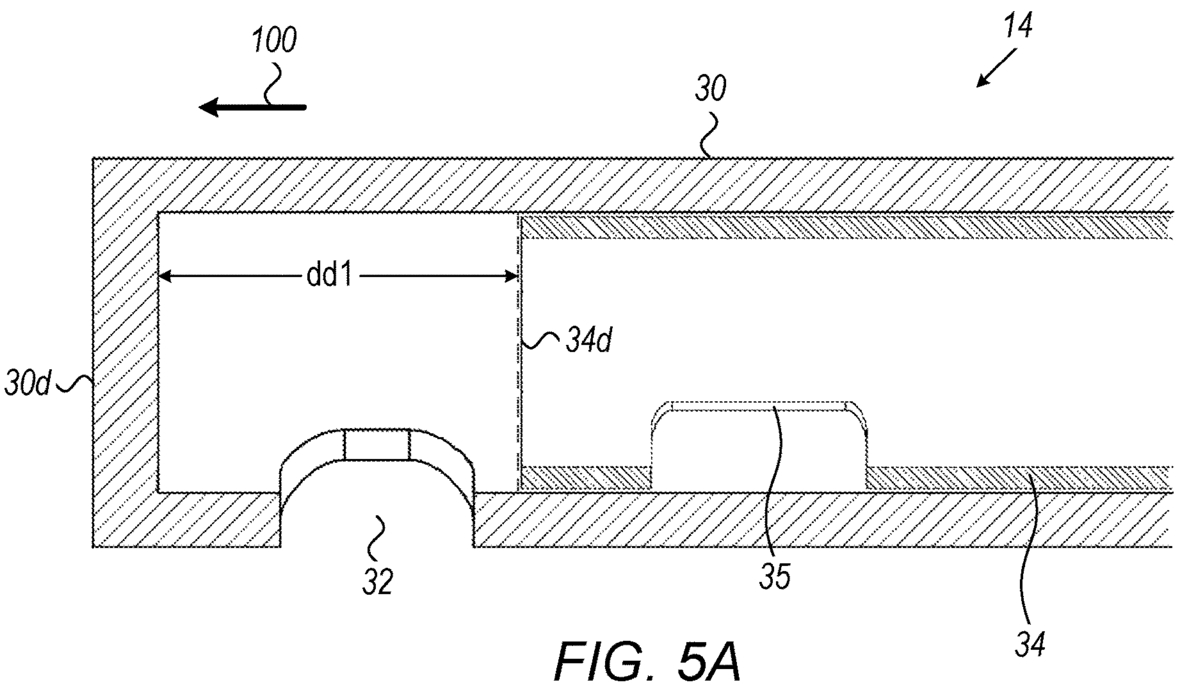
FIGS. 5A and 5B are cross sectional views of the cutting needle of the apparatus of FIG. 1 in an example cutting operation in accordance with the disclosure.
Figure 5B:
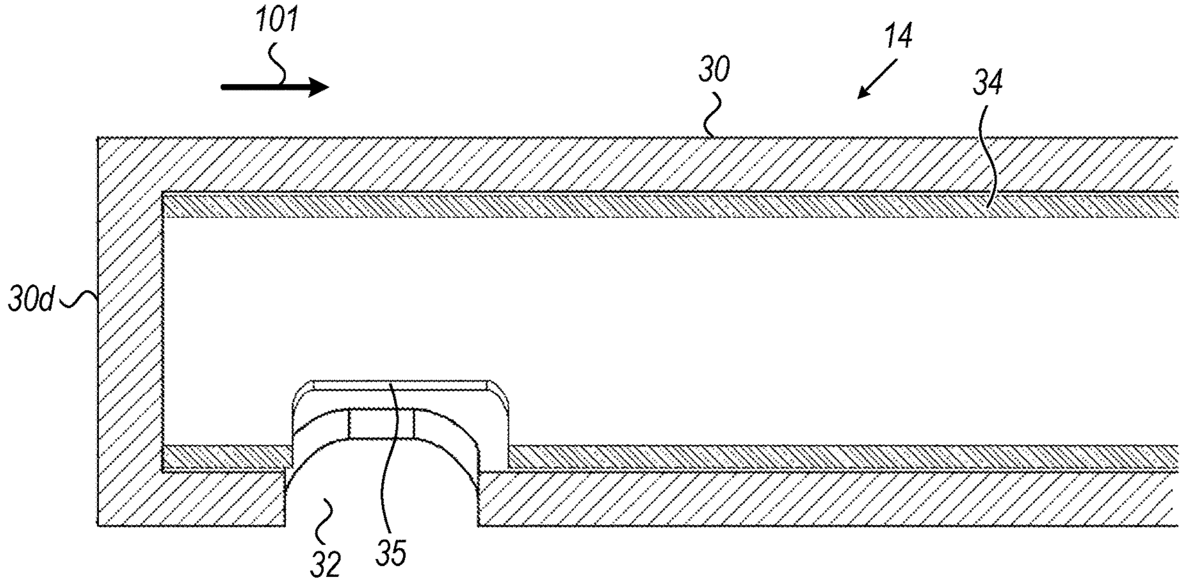

Turning also to FIG. 2B and FIG. 3 (the handpiece 10 separated into a cutting section 18 and a motor section 22), the needle 14, includes an external or outer needle 30 which extends from the needle housing 18, and is a hollow needle, with an aperture or window 32 at its distal end 30*d*. A hollow internal or inner needle 34 extends into the external needle 30, for example, to be coaxial with the external needle 30. The internal needle 34 includes a cutting aperture 35 at its distal end 34*d* (FIG. 5A). The internal needle 34 is designed to move linearly (e.g., back and forth) in the external needle 30, to move into and out of alignment with the aperture 32 of the external needle 30, to cut the vitreous humor (vitreous), as detailed below and shown in FIGS. 5A and 5B. The needle 14, for example, may be a needle commercially available from Johnson & Johnson Surgical Vision, Inc., Santa Ana, CA, USA.

The internal needle 34 is held in a fixed position in a bore 36*a* of a gripper 36. The holding in the fixed position is, for example, by a friction fit and/or adhesives, welds, and the like. The internal needle 34 extends proximally to a receiver 38, which supports the internal needle 34, as it moves linearly. A sealing member 38*x*, covers the distal end of the receiver 38, and is flush with the internal needle 34, sealing the receiver and aspiration line 40, from debris, which may enter the needle housing 18. The receiver 38 receives the aspiration line 40 (through an opening 19 in the housing 18), which is aligned, and in fluid communication, with the internal needle 34. When suction (from an external source to the now-connected handpiece 10, not shown) is pulled through the needle 14 via the aspiration line 40, aspirated material from the eye, e.g., vitreous material, is aspirated through internal needle 34 and into and through the aspiration line 40.

The external needle 30, at its proximal end 30*p* is held by an o-ring 46 in a sealing spacer 48. The sealing spacer 48 also seals the needle housing 18, for example, in an airtight and watertight manner, from the ambient environment.

A driver or drive mechanism 50 is formed by a barrel cam 52, bearing rings 53, and a shaft coupler 54, also referred to interchangeably herein as a shaft coupling element or a coupler. The driver 50, gripper 36 and receiver 38 form a drive system for the internal needle 34.

The barrel cam 52, bearing rings 53 and coupler 54 are connected by a drive shaft 56. The driver 50 is rotated by the motor shaft 74, which is received in a correspondingly shaped and dimensioned cut-out section 54*a* of a coupler 54 of the driver 50. For example, the cut-out section 54*a* may be press fit into the motor shaft 74 (FIG. 2B). The press fit is, for example, a frictional engagement in a male-female fit. This frictional engagement also results from the material of the coupler 54, which provides frictional forces in addition to those of the mechanical engagement of the motor shaft 74 in the cut-out portion 54*a* of the coupler 54, itself. For example, the coupler 54, including its cut-out portion 54*a* is of a resilient material, such as a silicon or thermoplastic polyurethane (TPU), of a hardness of approximately Shore A 80-90. This material of the coupler 54 provides increased frictional forces between the coupler 54 and the motor shaft 74, to create a frictionally snug engagement and coupling of the motor shaft 74 in the coupler 54, and a resultant attachment, connection or joining of the needle housing 18 to the motor housing 22.

The engagement between the coupler 54 and the motor shaft 74 results in frictional forces which allow for a substantially complete or complete transfer of the rotational motion from the motor shaft 74 to the driver 50, via the cut-out section 54*a*, with minimal if any slippage of the motor shaft 74 with respect to the coupler 54, and vice versa. These same frictional forces are low enough to provide low resistance when pulling the motor shaft in and out of the coupler, when engaging or separating the cutting section and the motor section from each other, for example, in a longitudinal direction in accordance with the longitudinal axis LA of the handpiece 10.

Figure 4:
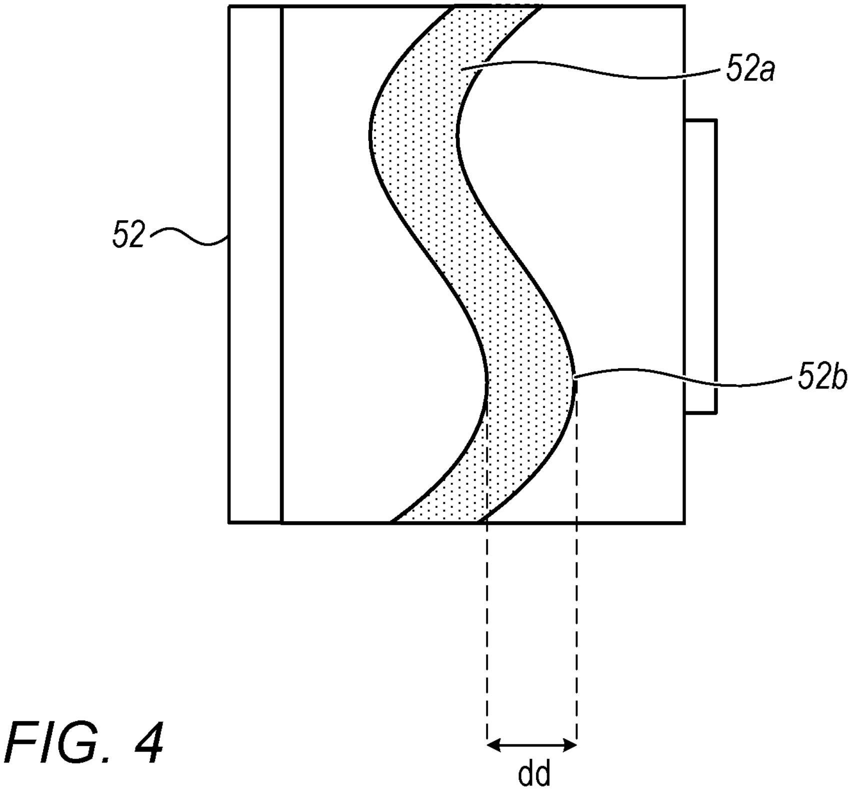
FIG. 4 is a side view of the barrel cam From FIGS. 2A, 2B and 3, in detail.

The barrel cam 52, as shown in FIG. 4, includes a track 52*a*, which receives a pin 58. The pin 58 is attached to the gripper 36. The barrel cam 52 translates rotational motion from the driver 50 to linear motion on the gripper 36, with the linear motion ultimately transferred to the internal needle 34, as it is held in place in the bore 36*a* of the gripper 36.

For example, in the barrel cam 52, the track 52*a* is curved 52*b* at various locations, which causes the gripper 36 to move a distance corresponding to the offset distance "dd" of the curved portion 52*b* of the track 52*a*. This distance dd is typically such that the aperture 35 of the internal needle 34, starts from a point proximal to the aperture 35 of the inner needle 34, moves distally into alignment with at least a portion of the aperture 32, so as to drawn in (suctioned) vitreous, and then pulls the internal needle 34 proximally, such that the aperture 35 is beyond the aperture 32, cutting the drawn in vitreous material, and allowing its aspiration through the needle 14 to the aspiration line 38. The distance of the curvature "dd" corresponds to the distance traveled by the internal needle 34. For example, the barrel cam 52 includes three curvatures 50*b* of distance "dd", corresponding to three aforementioned back and forth (e.g., linear) movements of the internal needle 34, on a single revolution of the barrel cam 52. The distance dd corresponds (e.g., is equal or approximately equal to) the travel distance dd1 (a linear distance) of the internal needle 34 and its aperture 35 (for example in the distal direction by the internal needle 34 in the direction of the arrow 100), as shown, for example, in FIG. 5A, with the cutting of vitreous in a return movement in the proximal direction by the internal needle 34, of the cutting cycle (indicated by the arrow 101) shown in FIG. 5B (with the vitreous having been pulled into the internal needle 34 via suction).

The bearing rings 53 include and outer fixed ring 53*a*, which mount in a collar 60 in slots 60*x* in a clamping arrangement. The rings 53 are separated by a spacer portion 60*s*. The outer rings 53*a* and inner rings 53*b* cooperatively support ball bearings 53*c* between the rings 53*a*, 53*b*, in aligned grooves 53*ax*, 53*bx*. The ball bearings 53*c* facilitate rotation of the inner rings 53*b*. The inner rings 53*b* each attach to the drive shaft 56 and rotate with the drive shaft 56.

The collar 60, at its head portion 60*h* attaches to a cut-out section 18*b* in the inner wall 18*a* of the needle housing 18 in a frictionally snug fit. This frictionally snug fit keeps the collar 60 in a fixed position in the housing 18, preventing the collar 60 from rotating in the housing. The cut-out portion 18*b* includes a transverse surface 18*c*, which serves as a distal limit of travel for the collar 60.

The cut-out portion 18*b* of the inner wall 18*a* extends over the head portion 60*h* of the collar 60 and terminates in a proximal edge 18*p* of the needle housing 18. This proximal edge 18*p* serves as a limit of distal travel for the motor housing 22. The head portion 60*h* of the collar 60 is, for example, of an outer diameter equal to or approximately equal to the inner diameter of the longitudinal surface 61*c* of the cut-out portion 18*b*, to facilitate the frictionally snug fit. Additional adhesives may be used to attach the collar 60 to the inner wall 18*a*/18*b* of the needle housing 18.

The collar 60 frictionally engages the bearing rings 53, for example, in a clamping manner, to maintain or otherwise hold the driver 50 in a fixed position in the needle housing 18, while allowing for rotation of the barrel cam 52, coupler 54, and drive shaft 56.

One or more rails 62, attached to the gripper 36 are, for example, parallel to the drive shaft 56. The rail 62 rides in a slot 63. The slot 63 is of an inner diameter larger than the outer diameter of the rail 62, to allow for linear (back and forth) movement (sliding) of the rail 62 in the slot 63. This movable arrangement of the rail 62 in the slot 63 maintains the position of the gripper 36 in the needle housing 18.

The collar 60 is, for example, a unitary cylindrical shaped piece (e.g., circular or rounded in transverse cross section. The collar 60 is rigid, for example, of a material such as metal or plastic.

The collar 60 includes shoulders 60*a*. The transverse surface 60*at* of the shoulders 60*a* serves as a distal limit of travel for the motor housing 22 when it is joined, attached or connected to the needle housing 18. An end portion 22*x* of the motor housing 22 extends distally, such that the transverse surface 80*t* of the first indentation 80 of the motor housing 22 abuts the transverse surface 60*at*, when the needle housing 18 and motor housing 22 are joined or otherwise connected or attached as a handpiece 10 for use.

The collar 60 includes an annular section 60*b*, extending proximally from the shoulders 60*a*, and which terminates at an outwardly protruding band 60*c*. The annular section 60*b*, at the band 60*c*, forms a snap fit with the circumferential groove 84 of the motor housing 22. The snap-fit locks the now-connected needle housing 18 to the motor housing 22. The annular section 60*b*, for example, optionally includes longitudinally extending slits or cut-outs 64, to allow for spring-like behavior to facilitate the aforementioned snap fit of the band 62*c* into a corresponding circumferential groove 84 of the motor housing 22 (which locks the cutting section/needle housing 18 in the motor section/motor housing 22).

The annular section 60*b* is, for example, of an outer diameter just slightly less than the inner diameter of an inner cavity 78 of the motor housing 22, to frictionally engage the inner wall 22*a* of the motor housing 22. The annular section 60*b* also includes longitudinally extending ridges (not shown), for receipt in correspondingly positioned and dimensioned grooves 82 in the motor housing 22, to prevent rotational movement of the needle housing 18, while the collar 60 is engaged in and with the motor housing 22.

Alternately, the annular section 60*b* may include outwardly protruding threads or a threaded section to engage a correspondingly configured inner wall 22*a* of the inner cavity 78. This screw arrangement maintains the needle housing 18 joined with the motor housing 22, in a manner allowing for manual separation of the needle housing 18 from the motor housing 22 by human hands, as the components 18, 22 are unscrewed from each other. In the case of the screw arrangement, the band 60*c* need not be present. Clips and other mechanical fasteners may also be used to lock the needle housing 18 to the motor housing 22.

The motor housing 22 houses a motor 70 in a chamber 72, a motor shaft 74, rotated by the motor 60, which extends from the motor 70. The chamber 72 with the motor 70 and motor shaft 74 are sealed, for example, in an airtight and watertight manner, from the ambient environment. The motor shaft 74 which extends distally into the inner cavity 78 is, for example, coated with the material of the cut-out portion 54*a* of the coupler 54 to provide the aforementioned frictional forces suitable for maintaining rotational motion transferred from the motor shaft 74, while also serving to cooperatively maintain the connection between the needle housing 18 and the motor hosing 22.

The motor housing 22 is such that its inner cavity 78 receives the coupler 54 (correspondingly configured with respect to the motor shaft 74 for coupling with the motor shaft 74) and the collar 60 of the needle housing 18 (for connecting the needle housing 18 to the motor housing 22). The motor 70 rotates the motor shaft 74, to transfer rotational motion to the driver 50, which subsequently translates the rotational motion into linear (e.g., back and forth) motion on the internal needle 34 at speeds sufficient to cut vitreous material in ophthalmic procedures, such vitrectomies, retinal procedures, cataract procedures, and the like.

A first indentation 80, extending proximally to a transverse surface 80*t* at the distal portion 22*x* of the motor housing 22, is dimensioned to receive the shoulders 60*a* of the collar 60 of the needle housing 18. The transverse surface 80*t*, for example, abuts the transverse surface 60*at* of the collar 60 at the shoulders 60*a*. The receiving is such that the motor housing 22 distal portion 22*x* (i.e., at its distal edge) abuts the proximal edge 18*p* of the needle housing 18, in a manner where, for example, the outer surfaces 18*y*, 22*y* of the needle housing 18 and the motor housing 22 are flush with each other.

A longitudinal groove 82 receives a correspondingly positioned (protruding) ridge (not shown) on the outer side of the annular section 60*b* of the collar 60. This receipt prevents rotational movement of the collar 60 in the motor housing 22. A circumferential groove 84 receives the protruding band 60*c* of the collar 60, for example, in a snap fit, as once the band 60*c* reaches the groove 84, it moves outward in a spring-like manner (due to the rigidity of the material of the collar 60, and the annular section 60*b* and band 60*c*), to seat in the circumferential groove 84. The seating results in an engagement force sufficiently maintains the needle housing 18 in the motor housing 22 in a locked, yet removably attachable, connection (attachment). However, this locking may also be broken manually upon disengaging or separating the needle housing 18 from the motor housing 22, allowing the needle housing 18 to be disposed of after use as part of the handpiece 10.

In operation, the needle housing 18 is connected or joined to the motor housing 22, such that the coupler 54, at its cut out section 54*a*, engages or couples to the motor shaft 74. The collar 50, at the annular section 60*b* and proximal band 60*c*, are pushed into the cavity 78 of the motor housing 22, until the band 60*c* snaps into the circumferential groove 84 of the motor housing, so that the band 60*c* seats in the circumferential groove 84, locking the needle housing 18 in the motor housing 22. Rotational movement on the needle housing 18 (as well as the motor housing 22) is prevented as the transverse ridge (not shown) on the collar 60, engages the transverse groove 82 in the inner wall 22*a* of the motor housing 22.

When separation or disengagement of the disposable needle housing 18 from the motor housing 22 is desired, such as when a procedure is complete or ended, the needle housing 18 and motor housing 22 are manually separated, by being pulled apart, such that manual separation force unlocks the band 60*c* from the circumferential groove 84, as the slits 64 allow for inward movement of the annular section 60*b*, and the motor shaft 74 is disengaged from, i.e., pulled out of, the coupler 54 (cut-out section 54*a*).

EXAMPLES

Example 1

A cutting section (18) for a vitrector handpiece (10), the cutting section (18) comprising: a housing (18) for being removably attachable from a motor section (22) of the vitrector handpiece (10); a cutting needle (14) extending from inside the housing (18) to outside of the housing (18); and, a drive system in communication with the cutting needle (14), the drive system configured for translating rotational motion from a driver (50) to linear motion of the cutting needle (14), the driver (50) including a coupler (54) for coupling with a shaft (74) of a motor (70) of the attachable motor section (22) in a frictional engagement, the frictional engagement providing frictional forces which: 1) allow for a substantially complete transfer of the rotational motion from the shaft (74) of the motor (70) to the driver (54) substantially free of slippage of the shaft (74) of the motor (70) with respect to the coupler (54), and 2) allow for the coupler (54) and the shaft (74) of the motor (70) to be manually joined or manually separated from each other.

Example 2

The cutting section of Example 1, wherein the coupling of the coupler (54) with the shaft (74) of the motor (70) attaches the housing (18) to the motor section (22).

Example 3

The cutting section of any of Example 1 or Example 2, wherein the coupler (54) includes a portion (54*a*) shaped and dimensioned to correspond to the shape and dimensions of the shaft (74) of the motor (70), the portion (54*a*) for receiving the shaft (74) of the motor (70).

Example 4

The cutting section of any of Example 1 to Example 3, wherein the portion (54*a*) of the coupler (54) receives the shaft (74) of the motor (70) in a male-female fit.

Example 5

The cutting section of any one of Example 1 to Example 4, wherein the portion (54*a*) of the coupler (54) includes a resilient material.

Example 6

The cutting section of any of Example 1 to Example 5, wherein the resilient material is selected from the group of silicon or thermoplastic polyurethane (TPU), and of a hardness of approximately Shore A 80-90.

Example 7

The cutting section of any of Example 1 to Example 6, wherein the cutting needle (14) comprises: an external needle (30) mounted to the housing (18), and, an internal needle (34), a portion of the internal needle (34) extending outside of the external needle (30), the internal needle (34) for moving in accordance with the linear motion from the drive system, the internal needle (34) for cutting tissue pulled into the external needle (30).

Example 8

The cutting section of any of Example 1 to Example 7, additionally comprising: a collar (60) intermediate the driver (50) and an inner wall (18*a*) of the housing (18), the collar (50) configured to engage the inner wall (18*a*) of the housing (18) and engage the driver (50), the collar (60) including an outwardly extending annular section (60*b*) for engagement in a corresponding cavity (78) of the motor section (22), for locking the housing (18) when attached to the motor section (22).

Example 9

The cutting section of any one of Example 1 to Example 8, additionally comprising a motor section (22), wherein the coupling of the coupler (54) with the shaft (74) of the motor (70) of the motor section (22) attaches the housing (18) to the motor section (22).

Example 10

A vitrector handpiece (10), comprising: a cutting section (18) comprising: a housing (18) for being removably attachable from a motor section (22) of the vitrector handpiece (10); a cutting needle (14) extending from inside the housing (18) to outside of the housing (18); and, a drive system in communication with the cutting needle (14), the drive system configured for translating rotational motion from a driver (50) to linear motion of the cutting needle (14), the driver (50) including a coupler (54) for coupling with a shaft (74) of a motor (70) of the removably attachable motor section (22) in a frictional engagement, the frictional engagement providing frictional forces which: 1) allow for a substantially complete transfer of the rotational motion from the shaft (74) of the motor (70) to the driver (50) substantially free of slippage of the shaft (74) of the motor (70) with respect to the coupler (54), and 2) allow for the coupler (54) and the shaft (74) of the motor (70) to be manually joined or manually separated from each other; and, a removably attachable motor section (22) including motor (70) the in communication with the shaft (74).

Example 11

The vitrector handpiece of Example 10, wherein the coupler (54) includes (54*a*) a portion shaped and dimensioned to correspond to the shape and dimensions of the shaft (74) of the motor (70), the portion (54*a*) for receiving the shaft (74) of the motor (70).

Example 12

The vitrector handpiece of any of Example 10 or Example 11, wherein the portion (54*a*) of the coupler (54) receives the shaft (74) of the motor (70) in a male-female fit.

Example 13

The vitrector handpiece of any of Example 10 to Example 12, wherein the portion (54*a*) of the coupler (54) includes a resilient material.

Example 14

The vitrector handpiece of any of Example 10 to Example 13, wherein the resilient material is selected from the group of silicon or thermoplastic polyurethane (TPU), and of a hardness of approximately Shore A 80-90.

Example 15

The vitrector handpiece of any of Example 10 to Example 14, wherein the cutting needle (14) comprises: an external needle (30) mounted to the housing (18), and, an internal needle (34), a portion of the internal needle (34) extending outside of the external needle (30), the internal needle (34) for moving in accordance with the linear motion from the drive system, the internal needle (34) for cutting tissue pulled into the external needle (30).

Example 16

The vitrector handpiece of any of Example 10 to Example 15, additionally comprising: a collar (60) intermediate the driver and an inner wall (18*a*) of the housing (18), the collar (60) configured to engage an inner wall (18*a*) of the housing (18) and engage the driver (50), the collar (60) including an outwardly extending annular section (60*b*) for engagement in a corresponding cavity (78) of the motor section (22), for locking the housing (18) when attached to the motor section (22).

Example 17

A method for using a vitrector handpiece (10), the method comprising: obtaining a cutting section (18) comprising: a housing (18) for being removably attachable from a motor section (22) of the vitrector handpiece (10); a cutting needle (14) extending from inside the housing (18) to outside of the housing (18); and, a drive system in communication with the cutting needle (14), the drive system configured for translating rotational motion from a driver (50) to linear motion of the cutting needle (14), the driver (50) including a coupler (54) for coupling with a shaft (74) of a motor (70) of the removably attachable motor section (22) in a frictional engagement, the frictional engagement providing frictional forces which: 1) allow for a substantially complete transfer of the rotational motion from the shaft (74) of the motor (70) to the driver (50) substantially free of slippage of the shaft (74) of the motor (70) with respect to the coupler (54), and 2) allow for the coupler (50) and shaft (74) of the motor (70) to be manually joined or manually separated from each other; and, coupling the housing (18) of the cutting section (18) to the motor section (22) in a removably attachable manner, including engaging the shaft (74) of the motor (70) in the coupler (54).

It will thus be appreciated that the examples described above do not limit the present disclosure to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A cutting section for a vitrector handpiece, the cutting section comprising:

a housing for being removably attachable from a motor section of the vitrector handpiece;

a collar frictionally fit into and extending past an inner wall of a proximal end of the housing, the collar including an outwardly extending annular section for engagement in a corresponding cavity of the motor section;

a cutting needle extending from inside the housing to outside of the housing; and a drive system in communication with the cutting needle, the drive system configured for translating rotational motion from a driver to linear motion of the cutting needle, the driver including a coupler for coupling with a shaft of a motor of the removably attachable motor section in a frictional engagement, the frictional engagement providing frictional forces which: 1) allow for a substantially complete transfer of the rotational motion from the shaft of the motor to the driver substantially free of slippage of the shaft of the motor with respect to the coupler, and 2) allow for the coupler and the shaft of the motor to be manually joined or manually separated from each other.

2. The cutting section of claim 1, wherein the coupling of the coupler with the shaft of the motor attaches the housing to the motor section.

3. The cutting section of claim 2, wherein the coupling of the coupler with the shaft of the motor of the motor section attaches the housing to the motor section.

4. The cutting section of claim 1, wherein the coupler includes a portion shaped and dimensioned to correspond to the shape and dimensions of the shaft of the motor, the portion for receiving the shaft of the motor.

5. The cutting section of claim 4, wherein the portion of the coupler receives the shaft of the motor in a male-female fit.

6. The cutting section of claim 4, wherein the portion of the coupler includes a resilient material.

7. The cutting section of claim 6, wherein the resilient material is selected from the group of silicon or thermoplastic polyurethane (TPU), and of a hardness of approximately Shore A 80-90.

8. The cutting section of claim 1, wherein the cutting needle comprises:

an external needle mounted to the housing, and an internal needle, a portion of the internal needle extending outside of the external needle, the internal needle for moving in accordance with the linear motion from the drive system, the internal needle for cutting tissue pulled into the external needle.

9. A vitrector handpiece, comprising:

a cutting section comprising:

a housing for being removably attachable from a motor section of the vitrector handpiece;

a collar frictionally fit into and extending past an inner wall of a proximal end of the housing, the collar including an outwardly extending annular section for engagement in a corresponding cavity of the motor section;

a cutting needle extending from inside the housing to outside of the housing; and a drive system in communication with the cutting needle, the drive system configured for translating rotational motion from a driver to linear motion of the cutting needle, the driver including a coupler for coupling with a shaft of a motor of the removably attachable motor section in a frictional engagement, the frictional engagement providing frictional forces which: 1) allow for a substantially complete transfer of the rotational motion from the shaft of the motor to the driver substantially free of slippage of the shaft of the motor with respect to the coupler, and 2) allow for the coupler and the shaft of the motor to be manually joined or manually separated from each other; and the removably attachable motor section including the motor in communication with the shaft.

10. The vitrector handpiece of claim 9, wherein the coupler includes a portion shaped and dimensioned to correspond to the shape and dimensions of the shaft of the motor, the portion for receiving the shaft of the motor.

11. The vitrector handpiece of claim 10, wherein the portion of the coupler receives the shaft of the motor in a male-female fit.

12. The vitrector handpiece of claim 10, wherein the portion of the coupler includes a resilient material.

13. The vitrector handpiece of claim 12, wherein the resilient material is selected from the group of silicon or thermoplastic polyurethane (TPU), and of a hardness of approximately Shore A 80-90.

14. The vitrector handpiece of claim 9, wherein the cutting needle comprises:

an external needle mounted to the housing, and an internal needle, a portion of the internal needle extending outside of the external needle, the internal needle for moving in accordance with the linear motion from the drive system, the internal needle for cutting tissue pulled into the external needle.

15. A method for using a vitrector handpiece, the method comprising:

obtaining a cutting section comprising:

a housing for being removably attachable from a motor section of the vitrector handpiece;

a collar frictionally fit into and extending past an inner wall of a proximal end of the housing, the collar including an outwardly extending annular section for engagement in a corresponding cavity of the motor section;

a cutting needle extending from inside the housing to outside of the housing; and a drive system in communication with the cutting needle, the drive system configured for translating rotational motion from a driver to linear motion of the cutting needle, the driver including a coupler for coupling with a shaft of a motor of the removably attachable motor section in a frictional engagement, the frictional engagement providing frictional forces which: 1) allow for a substantially complete transfer of the rotational motion from the shaft of the motor to the driver substantially free of slippage of the shaft of the motor with respect to the coupler, and 2) allow for the coupler and shaft of the motor to be manually joined or manually separated from each other; and coupling the housing of the cutting section to the motor section in a removably attachable manner, including engaging the shaft of the motor in the coupler.

* * * * *